United States Patent
Furuta et al.

(10) Patent No.: US 9,958,563 B2
(45) Date of Patent: May 1, 2018

(54) RADIATION MEASUREMENT METHOD AND DEVICE

(71) Applicants: OCHANOMIZU UNIVERSITY, Tokyo (JP); HITACHI, LTD., Tokyo (JP)

(72) Inventors: Etsuko Furuta, Tokyo (JP); Yuka Kato, Tokyo (JP); Kiyoshi Ogiwara, Tokyo (JP)

(73) Assignees: OCHANOMZU UNIVERSITY, Tokyo (JP); Hitachi, Ltd., Tokyo (JP)

( * ) Notice: Subject to any disclaimer, the term of this patent is extended or adjusted under 35 U.S.C. 154(b) by 0 days. days.

(21) Appl. No.: 15/327,080

(22) PCT Filed: Jul. 17, 2015

(86) PCT No.: PCT/JP2015/070562
§ 371 (c)(1),
(2) Date: Jan. 18, 2017

(87) PCT Pub. No.: WO2016/013517
PCT Pub. Date: Jan. 28, 2016

(65) Prior Publication Data
US 2017/0160409 A1    Jun. 8, 2017

(30) Foreign Application Priority Data

Jul. 23, 2014  (JP) ................................ 2014-150178

(51) Int. Cl.
*G01T 7/02*   (2006.01)
*G01T 1/167*  (2006.01)
(Continued)

(52) U.S. Cl.
CPC ........... *G01T 7/02* (2013.01); *G01N 33/0055* (2013.01); *G01T 1/167* (2013.01); *G01T 1/20* (2013.01); *G01T 1/203* (2013.01); *G01T 7/08* (2013.01)

(58) Field of Classification Search
CPC ....... G01N 33/0055; G01T 1/167; G01T 1/20; G01T 1/203; G01T 7/02; G01T 7/08
See application file for complete search history.

(56) References Cited

U.S. PATENT DOCUMENTS 3,763,371 A * 10/1973 Reunanen ............. G01T 1/2045
                                              250/252.1
3,819,489 A *  6/1974 Kronick ................... C12Q 1/04
                                              250/304

(Continued)

FOREIGN PATENT DOCUMENTS

EP    2930538 A1    10/2015
JP   57-179680     11/1982

(Continued)

OTHER PUBLICATIONS

English translation of International Preliminary Report on Patentability dated Feb. 2, 2017 in connection with PCT/JP2015/070562.

(Continued)

*Primary Examiner* — Marcus Taningco
(74) *Attorney, Agent, or Firm* — Cooper & Dunham LLP

(57) ABSTRACT

A solid scintillator member is provided in the internal space of a container. The scintillator member is an aggregate of a plurality of pellets. The internal space also confines a gas produced through the vaporization of a liquid sample containing a radioactive substance. When radiation emitted from a plurality of particles within the gas reaches the scintillator member, light is generated. That light is detected by a pair of photomultipliers. A plurality of particles may be (Continued)

produced outside of the container and introduced into the container.

13 Claims, 14 Drawing Sheets

(51) Int. Cl.
    *G01T 1/20*     (2006.01)
    *G01T 1/203*     (2006.01)
    *G01N 33/00*     (2006.01)
    *G01T 7/08*     (2006.01)

(56) References Cited

U.S. PATENT DOCUMENTS

| | | | | |
|---|---|---|---|---|
| 3,844,894 A | * | 10/1974 | Kronick | C12Q 1/00 422/83 |
| 4,019,864 A | * | 4/1977 | Saito | G01N 31/005 250/303 |
| 4,495,420 A | * | 1/1985 | Chudy | G01T 1/003 250/328 |
| 4,755,471 A | | 7/1988 | Saito et al. | |
| 5,783,828 A | * | 7/1998 | Pacenti | G01T 1/205 250/361 R |
| 6,159,427 A | * | 12/2000 | Kherani | G01N 33/18 422/82.01 |

FOREIGN PATENT DOCUMENTS

| | | |
|---|---|---|
| JP | 2007-178336 | 7/2007 |
| JP | 2007-218827 | 8/2007 |
| JP | 2009-294089 | 12/2009 |
| WO | WO2014/088046 A1 | 6/2014 |

OTHER PUBLICATIONS

International Search Report in connection with PCT.JP2015/070562.

* cited by examiner

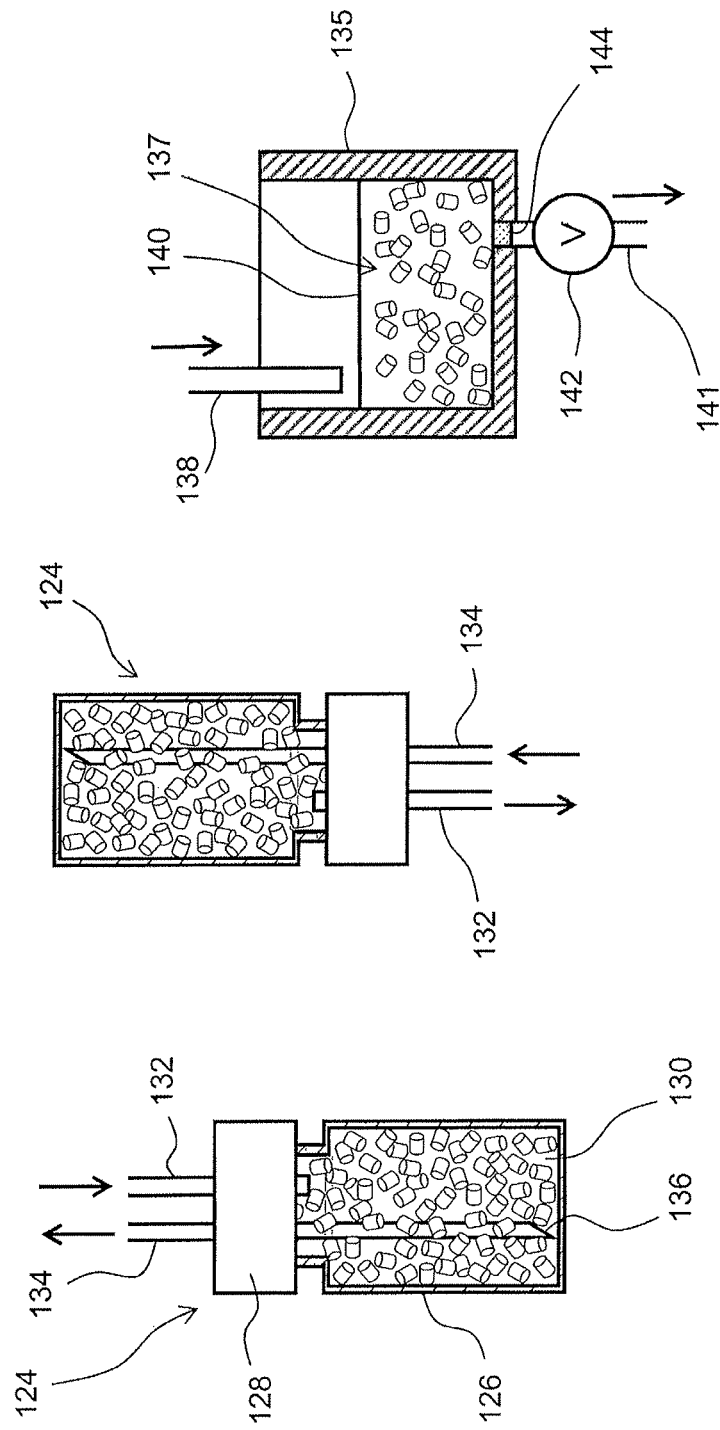

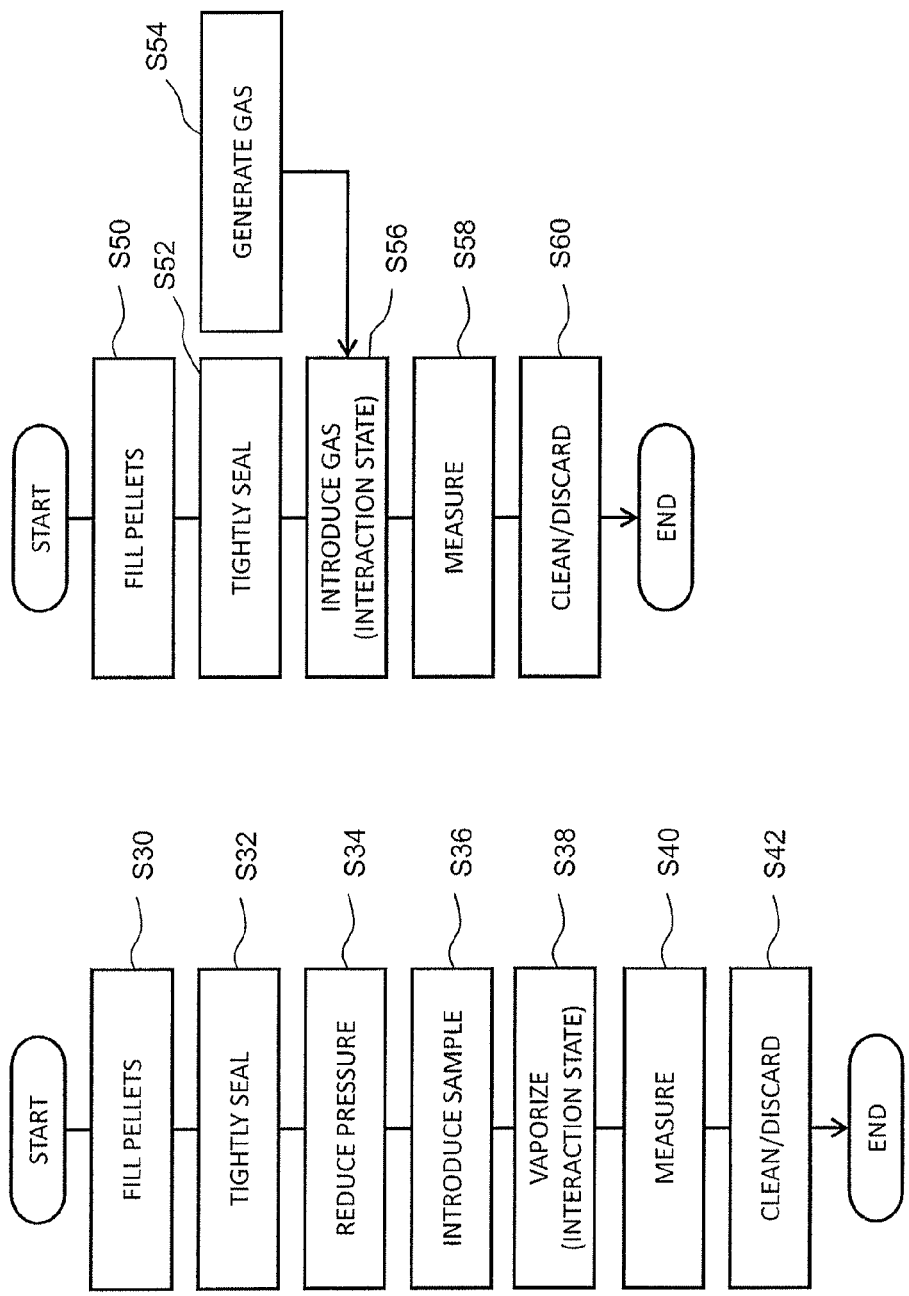

RADIATION MEASUREMENT METHOD AND DEVICE

TECHNICAL FIELD

The present disclosure relates to a radiation measurement method and a radiation measurement apparatus, and in particular, to a radiation measurement method and a radiation measurement apparatus suitable for measurement of low-energy β-rays.

BACKGROUND

Several methods are known as radiation measurement methods using scintillators. A solid scintillator method is a method of measuring radiation using a solid scintillator (for example, a plastic scintillator). In general, with this method, it is difficult to measure low-energy radiation; that is, radiation with short maximum ranges (reaching distances). For example, a method may be considered in which a liquid drop of a liquid sample containing tritium is placed on a surface of a scintillator plate or the liquid drop is spread to form a liquid layer on the surface, and β-ray emitted from tritium is detected in this state. However, the maximum range of the β-ray emitted from tritium is only about 5 mm in the air, and about 6 μm in water. Therefore, the β-ray emitted from the tritium is significantly attenuated (self-absorption) during the process of passing through the liquid sample itself. Because of this, an amount of β-ray exiting from the liquid sample would be very small, and sufficient light emission could not be generated on the scintillator plate.

A liquid scintillator method is a method of measuring radiation (in particular, β-rays) emitted from a liquid sample using a liquid scintillator. In this method, a liquid sample containing a radioactive substance is added to the liquid scintillator. In this case, the liquid scintillator exists near the periphery of the radioactive substance, and emits light due to the β-ray emitted from the radioactive substance. In this method, however, a problem occurs in which the spectrum changes due to chemical quenching. In addition, it takes a great effort to treat organic waste solutions generated after the measurement.

Patent Literature 1 discloses application of a hydrophilic treatment on a surface of a plastic scintillator, to adhere the liquid sample thereon. Patent Literature 2 discloses a tritium detection apparatus. In this apparatus, a liquid layer is formed by cooling water vapor containing tritium, and β-rays emitted from the liquid layer are detected. The structure, however, causes the above-described problem of self-absorption.

CITATION LIST

Patent Literature

Patent Literature 1: WO 2014/088046
Patent Literature 2: JP 2007-218827 A

SUMMARY

Technical Problem

An advantage of the present disclosure lies in realizing a new radiation measurement method for a liquid sample, using a solid scintillator. Another advantage of the present disclosure lies in precise measurement of low-energy radiations. Yet another advantage of the present disclosure lies in precise measurement of the low-energy radiation without the use of liquid scintillators and without being affected or significantly affected by the self-absorption.

Solution to Problem (1) According to one aspect of the present disclosure, there is provided a radiation measurement method comprising: a state formation step in which a liquid sample containing a radioactive substance is vaporized to generate gas containing a plurality of particles, and the gas is confined along with a solid scintillator member in a space isolated from the outside environment, to form an interaction state; and a detection step in which light generated on the scintillator member due to a radiation from the plurality of particles in the interaction state is detected.

In the above-described configuration, by the vaporization of the liquid sample, gas (evaporation-product gas) is generated. The gas is a group of a large number of particles (evaporation-product particles). All or a part of the large number of particles contain a radioactive substance. The gas generated by the vaporization is confined in a space (reaction space) isolated from the outside environment, along with a solid scintillator member. With this process, a state is formed in which an interaction occurs between the scintillator member and a plurality of particles (more precisely, a state where probability of occurrence of the interaction is significantly increased). This state may be referred to as an "interaction state" or a "reaction promoted state." A part of the plurality of particles contact (desirably, adhere onto) a surface of the scintillator member, and, in this state, when radiation from the contacted particle reaches the scintillator member, light emission (scintillation) is caused on the scintillator member. In addition, another part of the plurality of particles may be considered to move within the space. When a radiation from moving particles reaches the scintillator member also, light emission is generated. In this case, particles at positions closer to the surface of the scintillator member would cause larger light emissions. These light emissions are detected by a detector.

According to a radiation measurement method of the present disclosure, in comparison to a case where the radiation emitted from the liquid sample is detected without any processing, because the problem of the self-absorption is not caused or can be significantly reduced, the detection sensitivity (or a light conversion efficiency) of the radiation can be improved. In particular, low-energy radiation can be detected with high sensitivity.

Alternatively, various conditions may be determined such that a larger number of particles adhere onto the surface of the scintillator member. For example, a treatment to facilitate adhesion of the particles may be applied on the surface of the scintillator member, or a temperature of the scintillator member may be manipulated. Alternatively, an electrical attraction force may be utilized. Desirably, a form or a structure of the scintillator member is determined in such a manner that a larger number of particles contact the surface of the scintillator member or are positioned near the surface. For example, a large number of gaps may be formed inside the scintillator member, with a size of an individual gap determined in consideration of the maximum range of the radiation (desirably, equivalent to or less than the maximum range). Alternatively, in order to increase the stopping distance, other gases may be discharged from inside the reaction space. The radioactive substance is, for example, tritium that emits a low-energy β-ray. Alternatively, the radioactive substance may be other β-ray nuclides. So long as the above-described method can be applied, a nuclide which generates another type of radiation (for example, an α-ray emitting nuclide such as radon or thoron) may be set as a measurement target.

The above-described process of vaporization is a process for generating particles. Normally, the generated particles are gas molecules (or a coagulation thereof). The vaporization may be caused inside the reaction space, or the vaporization may be caused outside of the reaction space and the particles generated by the vaporization may be introduced into the reaction space. The vaporization is typically caused by evaporation of the liquid sample. Alternatively, ultrasound vibration or other particulate generation means may be employed. In either case, in place of measuring the radiation from the liquid sample itself, the liquid sample is phase-transitioned to gas or a similar state and the measurement is executed, so that the problem of self-absorption of the radiation can be resolved or reduced, and, as a result, a high sensitivity measurement can be realized. In the present method, a solid scintillator member is used, and the liquid scintillator is not used. Because of this, the problem of spectrum change due to chemical quenching can be avoided, and treatment of organic waste solutions or the like becomes unnecessary.

According to another aspect of the present disclosure, the scintillator member has a gap structure including a plurality of gaps that can capture the plurality of particles. With the gap structure, a surface area of the scintillator member (an area of a surface receiving the radiation) can be increased. With such a configuration, the probability of occurrence of interaction between the scintillator member and the plurality of particles can be increased. Conversely, it is desirable to determine the form and the structure of the scintillator member such that the surface area of the scintillator member is increased. For example, a porous structure or a sponge structure may be employed. Alternatively, the scintillator member may be configured as a collective structure of many elements. In this case, the form and the size of the individual element are desirably determined in such a manner that a large number of gaps are formed inside the collective structure. The form of individual scintillator element may be unified, or scintillator elements having various shapes and sizes may be used.

According to another aspect of the present disclosure, a container having an internal space serving as the space is used, the scintillator member is a collective structure of a plurality of scintillator elements filled in the container, and the collective structure has, as the gap structure, a flow path network through which the gas flows. According to such a configuration, by the filling of the container with the plurality of scintillator elements in the container, a collective structure having a form matching the form of the internal space of the container can be naturally formed, and, at the same time, a flow path network through which the gas flows or in which the gas remains can be naturally formed inside the space. When the form of the scintillator member is along the form of the internal space of the container, an amount of dead space can be reduced and the detection efficiency can be improved. As an alternative configuration, a structure may be considered in which a gas sample which is not caused by vaporization is confined in the container along with the collective structure having the gap structure. In this case also, light emission is caused in each scintillator element by the radiation from the radioactive substance in the gas sample.

According to another aspect of the present disclosure, the state formation step comprises: a collective structure filling step in which the plurality of scintillator elements are introduced into the container; a sample introduction step in which the liquid sample is introduced into the container; a tightly sealing step in which the container into which the plurality of scintillator elements and the liquid sample are introduced is set to a tightly sealed state; and a vaporization step in which vaporization of the liquid sample is caused in the container in the tightly sealed state. According to such a configuration, after both the plurality of scintillator elements and the liquid sample are introduced into the container and the container is set to a tightly sealed state, the gas is generated by the vaporization of the liquid sample in the container. The gas naturally enters the plurality of gaps existing inside the scintillator member, and the scintillator member is set under the gas atmosphere. In other words, in the container, a mixture state or a blended state of the scintillator member and the gas is formed. According to another aspect of the present disclosure, the vaporization step comprises a heating step in which the hollow container is heated. By the heating process, evaporation (in some cases, boiling) of the liquid sample can be promoted. Desirably, heating is applied in such a manner that a temperature of the scintillator member does not exceed an upper limit of the temperature. Alternatively, a scintillator member having heat endurance may be used. According to another aspect of the present disclosure, the method further comprises a step of naturally evaporating the liquid sample in the container. According to another aspect of the present disclosure, the method further comprises, after the detection step, a cleaning step in which the scintillator member is cleaned. According to such a configuration, the scintillator member can be reused.

(2) According to another aspect of the present disclosure, there is provided a radiation measurement apparatus comprising: a vaporizer unit that vaporizes a liquid sample containing a radioactive substance to generate gas containing a plurality of particles; a container that stores a solid scintillator member and the gas; and a detector that detects light generated on the scintillator member due to a radiation from the plurality of particles.

The vaporizer unit is a unit which vaporizes the liquid sample in the container to generate gas or a unit that vaporizes the sample outside the container to generate the gas. The former concept includes, in addition to a structure to actively generate gas, a structure that contributes to natural evaporation of the liquid sample in the container. In the case of the latter, a structure for introducing the gas into the container is provided. In either case, the above-described structure causes a phase transition of the sample from liquid to gas (and a similar state thereof), avoids or reduces influences of the sample itself on the radiation (that is, the self-absorption), and thereby facilitates reaching of the radiation from the radioactive substance to the scintillator member. Because the scintillator member and the gas exist together in the container, a state in which the plurality of particles contact or are in close proximity to the surface of the scintillator member is naturally formed. When the radiation emitted from these particles reaches the scintillator member, interaction therebetween is caused, and light is emitted from the scintillator member. The light is then detected by the detector. Desirably, the measurement is executed in a state where no gas enters or exits from the container, but it is also possible to execute the measurement in a state where the gas is continuously supplied.

According to another aspect of the present disclosure, the scintillator member is a collective structure of a plurality of scintillator elements filled in the container. According to such a configuration, a collective structure having the same form as a form of the internal space of the container can be easily formed. It is possible to avoid generation of an unnecessarily large space within the internal space. According to another aspect of the present disclosure, each of the scintillator elements has a form that forms a plurality of gaps within the collective structure in a formed state of the collective structure. As such a form, various forms may be employed such as a circular column, a sphere, and an ellipsoid. According to another aspect of the present disclosure, each of the scintillator elements comprises a plastic scintillator. According to another aspect of the present disclosure, the vaporizer unit is a unit that vaporizes the liquid sample at an inside of the container to generate the gas. When a liquid sample of a relatively small amount is introduced from an upper opening of the container after the collective structure is formed in the container, the liquid sample would adhere onto the surface of the plurality of scintillator elements, and natural vaporization of the liquid sample can be promoted. In this case, it is also possible to understand that the container and the collective structure under the normal temperature form the vaporizer unit. Alternatively, a vaporizer unit may be conceptualized as a structure including a pipet for dropping a predetermined amount of liquid sample to the container storing the collective structure. According to another aspect of the present disclosure, the vaporizer unit is a unit that vaporizes the liquid sample at an outside of the container to generate the gas, and a mechanism is provided that introduces into the container the gas generated at the outside of the container.

BRIEF DESCRIPTION OF DRAWINGS

FIG. 14 is a diagram showing a first example configuration of a cleaning method.

FIG. 15 is a diagram showing a second example configuration of a cleaning method.

FIG. 16 is a diagram showing a third example configuration of a cleaning method.

FIG. 17 is a flowchart showing a second configuration of a radiation measurement method according to an embodiment of the present disclosure.

FIG. 18 is a flowchart showing a third configuration of a radiation measurement method according to an embodiment of the present disclosure.

DESCRIPTION OF EMBODIMENTS

An embodiment of the present disclosure will now be described with reference to the drawings.

Figure 1:
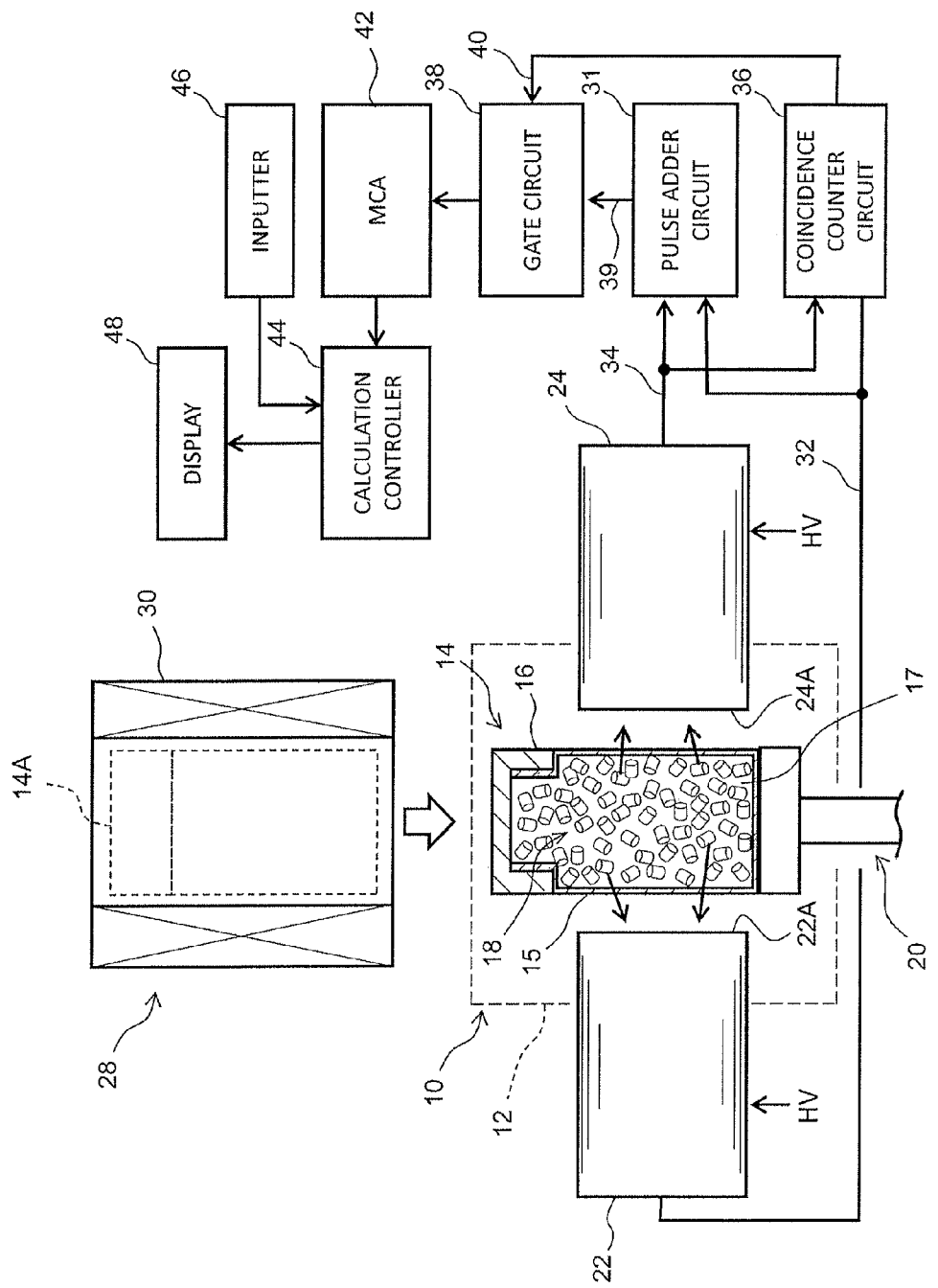
FIG. 1 is a conceptual diagram showing a radiation measurement apparatus according to an embodiment of the present disclosure.

FIG. 1 shows a radiation measurement apparatus according to an embodiment of the present disclosure, and is a block diagram showing an overall structure of the radiation measurement apparatus. A radiation measurement apparatus according to the embodiment of the present disclosure is an apparatus for measuring a concentration of a radioactive substance within a liquid sample or the like. Examples of the radioactive substance include nuclides such as H-3 (that is, T) and C-14. These nuclides are low-energy β-ray emitting nuclides. Alternatively, other β-ray emitting nuclides may be set as the detection target or other types of radiation may be detected. In the present embodiment, a liquid sample is a measurement target. Examples of the liquid sample include samples which become gas from liquid under normal temperatures, which may be, for example, water containing HTO.

In FIG. 1, a measurement unit 10 includes a measurement chamber 12. The measurement chamber 12 is a space surrounded by members that block radiation from the outside, and is set as a dark room. In FIG. 1, a container 14 is provided in the measurement chamber 12. On respective sides of the container 14, a pair of photomultiplier tubes (PMT) 22 and 24 are provided. The photomultiplier tubes 22, 24 serve as optical detectors.

The container 14 comprises a container body 15 and a lid 16. The container body 15 is formed from a transparent material, examples of which include glass, plastic, and the like. The container 14 is a vial, and functions as a reaction container. An opening provided on an upper part of the container body 15 is sealed by the lid 16 in a manner to allow opening and closing thereof. A screw structure is provided on each of the opening and the lid 16.

The lid 16 is formed from, for example, plastic, and has a milky white color. Alternatively, the lid 16 may be formed from a transparent material. As will be described below, in order to prevent occurrence of leakage from the container 14; that is, in order to set an internal space 17 to be an airtight space, a seal structure is desirably employed for the container 14. The internal space 17 functions as a vaporization space in the present embodiment, as will be described below.

In the internal space 17, a scintillator member 18 is stored and placed. The scintillator member 18 is a member that has a scintillation function in which light is emitted upon receiving radiation (β-ray in the present embodiment). In the present embodiment, the scintillator member 18 is formed as a collective structure of a plurality of pellets. Specifically, a plurality of pellets are filled in the container 14 and the internal space 17 is filled with the pellets. The collective structure of the plurality of pellets forms the scintillator member 18. Each pellet has, for example, a circular column shape, and is formed from a plastic scintillator. A plurality of gaps are created inside the scintillator member 18; that is, inside the collective structure, and function as a flow path network. For a material and a form of each scintillator element forming the collective structure, various materials and forms may be employed.

The internal space 17 is a space isolated from the outside environment. In the space, along with the scintillator member 18, gas generated from a liquid sample is confined. The gas is a group of a large number of particles. Specifically, prior to placing the container 14 in the measurement unit 10, a predetermined amount of the liquid sample is introduced in the container 14. By evaporation of the liquid sample, gas serving as sample gas is generated, and confined in the internal space 17. Alternatively, in order to prevent re-liquefaction of the gas, a temperature of the container 14 may be controlled during a transport process of the container 14 and in the measurement chamber 12. As an alternative to active heating, natural vaporization in the container may be utilized. In either way, it is desirable to determine a vaporization condition and an amount of injection such that sufficient vaporization occurs.

In the present embodiment, the gas generated by the vaporization of the liquid sample is water vapor. The water vapor contains a plurality of radioactive particles, each of which is a water molecule made of HTO or a coagulation thereof. Among the large number of particles, a part thereof can be considered to contact or adhere on the surface of the scintillator member 18, and another part thereof can be considered to float within the internal space 17. When a $\beta$-ray emitted from individual particle reaches the scintillator member, light emission is created. The light is then detected by the pair of photomultiplier tubes 22 and 24.

According to the present embodiment, because the liquid sample can be made into particulates or transformed to gas, and radiation emitted from individual particulate can be detected, an advantage can be obtained in that the above-described problem of self-absorption can be avoided or significantly reduced. Because the gas reaches everywhere outside and inside the scintillator member; that is, because the surface of the scintillator member is completely surrounded by the gas, the light emission efficiency can be improved. Further, an advantage can be obtained in that the problem of chemical quenching and the problem of the organic waste solution treatment, which are significant problems when the liquid scintillator is used, can be avoided. As will be described later, according to the present embodiment, a maximum energy of the $\beta$-ray can also be measured. In addition, as will be described below, it is also possible to clean the plurality of pellets that are once used, and reuse the pellets. In this case also, normally, the reuse may be realized with a typical cleaning process, and no complex waste solution treatment is required.

In FIG. 1, a heater unit 28 is a station which applies heating on the container before the container 14 is sent to the inside of the measurement chamber 12. The heater unit 28 has a space for receiving the container, and a container provided within this space is shown with a reference numeral 14A. The heater unit 28 in the present embodiment comprises a heater 30. Alternatively, other heating means may be employed. The method of vaporization is not limited to heating. In either way, it is desirable to apply the vaporization process to create particles (particulates). For the heating, it is desirable to heat the sample at a temperature lower than an upper limit temperature of the plastic scintillator. For example, the sample may be heated at 60° C. Alternatively, a plastic scintillator having superior heat endurance may be used. When evaporation of the liquid sample is caused while setting the internal space 17 of the container 14 to be an airtight space, an internal pressure of the container 14 would be increased. In this case, the motion of the particles becomes intense, and thus, a contact probability or an adhesion probability of the particles onto the surface of the scintillator member can be improved. Alternatively, the pressure inside the container 14 may be reduced before the liquid sample is introduced into the container 14, to provide advance protection against the increase of the pressure due to the heating. In this case, it can be considered that the maximum range of the radiation would be increased. In either case, desirably, the internal space 17 of the container 14 is tightly sealed with high reliability, in order to prevent leakage of the particles produced inside the container 14 to the outside environment.

Pulse signals 32 and 34 which are output from the pair of photomultiplier tubes 22 and 24 are sent to a pulse adder circuit 31 and a coincidence counter circuit 36. The pulse adder circuit 31 adds or combines the two pulse signals 32 and 34, to produce a single output signal. The output signal thereof is an output pulse 39. The coincidence counter circuit 36 is a circuit which outputs a gate signal 40 only when the two pulse signals 32 and 34 are simultaneously obtained. A gate circuit 38 allows the pulse 39 from the pulse adder circuit 31 to pass only during a gate period which is defined by the gate signal 40. In this manner, coincidence counting can be realized.

Signal processor circuits provided after the gate circuit 38 are omitted in the figures. A multi-channel analyzer (MCA) 42 is a processor that produces a spectrum by executing a pulse count for each individual energy channel. Data of the spectrum are sent to a calculation controller 44. The calculation controller 44 is formed from, for example, a personal computer. The calculation processor 44 has various calculation functions described below, and also executes operation control of the structures shown in FIG. 1. An inputter 46 is connected to the calculation controller 44, and a display 48 is connected to the calculation controller 44.

A container transport mechanism 20 is a mechanism which transports the container 14, and includes an elevator mechanism. In FIG. 1, the container 14 is placed on a base of the elevator mechanism. The base is a member that moves up and down. In the present embodiment, the container 14 is sent into the heater unit 28 prior to the measurement, by the container transport mechanism 20. In FIG. 1, the heater unit 28 is positioned above the measurement unit 10, but this is merely exemplary, and the heater unit 28 may be provided at any desired position. Alternatively, a cooler unit which cools the container after the measurement may be separately provided, or, as will be described later, a cleaning unit which cleans the scintillator member 18 after the measurement may be separately provided. The pair of photomultipliers 22 and 24 are placed in such a manner that two light-receiving surfaces 22A and 24A of the two photomultiplier tubes 22 and 24 are as proximate to the surface of the container 13 as possible without contacting the surface.

According to the structure shown in FIG. 1, a plurality of gas particles generated from the liquid sample are confined along with the scintillator member 18 in the internal space 17 which is isolated from the outside environment. With such a configuration, an interaction state; that is, a state in which the occurrence probability of scintillation is increased, is formed. With this configuration, an advantage can be obtained in that $\beta$-ray, in particular, low energy $\beta$-ray, can be measured with a high sensitivity without being affected or without being significantly affected by the problem of the self-absorption which occurs in the sample itself.

Figure 2:
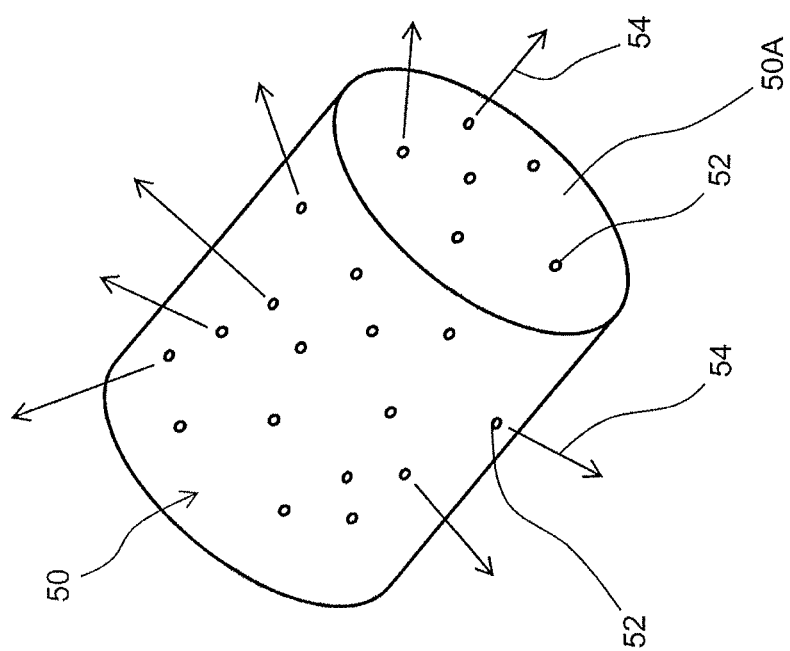
FIG. 2 is a perspective diagram showing a pellet to which particles are adhered.

FIG. 2 shows a first example configuration of the scintillator member. Specifically, FIG. 2 shows a pellet 50 serving as a scintillator element. The pellet 50 in the example configuration has a circular column shape. On a surface 50A of the pellet 50, a plurality of particles 52 are adhered. The particles 52 are, for example, formed from HTO. When β-ray emitted from T (tritium) in the particles enters the pellet 50, light emission is caused thereon. With this process, light 54 is emitted to the outside of the pellet 50.

Figure 3:
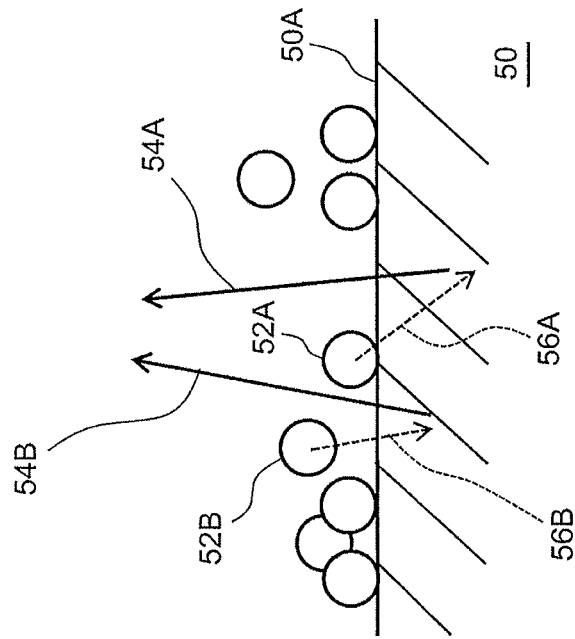
FIG. 3 is a diagram for explaining light emission by a radiation emitted from adhered particles and floating particles.

FIG. 3 is an enlarged cross sectional diagram of the surface 50A of the pellet 50. In the state shown in FIG. 3, several particles are adhered on the surface 50A, and several particles exist at positions distanced from the surface 50A. For example, when β-ray 56A is emitted from an adhered particle 52A and enters the pellet 50, scintillation is caused, and light 54A is emitted. In the case that a β-ray 56B from a particle 52B positioned near the surface 50A reaches the pellet 50 also, scintillation is caused and light 54B is emitted to the outside. Because the sample is transformed from liquid to gas, the problem of self-absorption of the β-ray by the sample itself can be significantly reduced.

When the pellets of the scintillator member emit light, a large amount of light emission is obtained by the scintillator member as a whole. It is desirable to suitably determine the form of the container such that more light generated in the container reaches the pair of light-receiving surfaces, and to suitably use a light reflective member. Even if a part of the particles are liquefied (condensed) on the surface of the pellet, if the percentage thereof is not large, a superior detection efficiency compared to the Comparative Example to be described below can be obtained.

Figure 4:
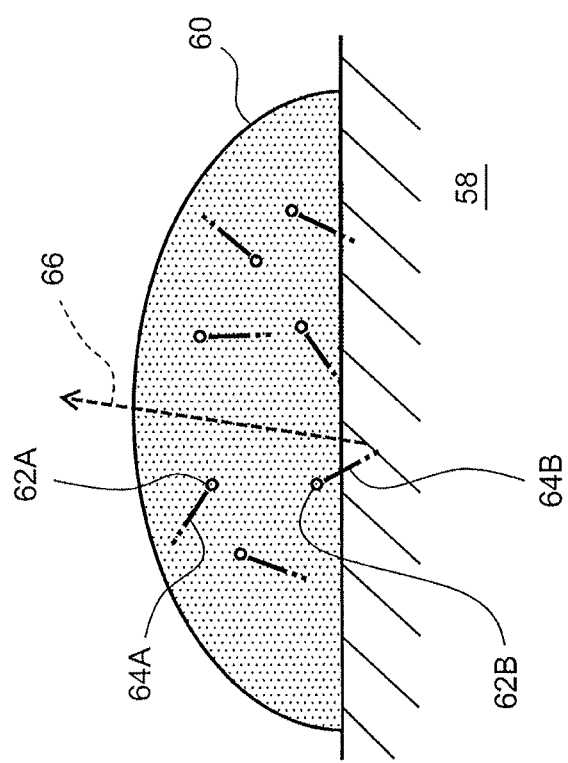
FIG. 4 is a diagram for explaining a comparative example.

FIG. 4 shows a Comparative Example. A liquid drop 60 is placed on a surface of a scintillator plate 58. The liquid drop 60 is the liquid sample, which includes tritium 62A and 62B which are radioactive substances. When β-ray 64A is emitted from the tritium 62A, the β-ray 64A would be significantly attenuated in the liquid drop 60 due to the attenuation action of the liquid drop 60 itself. That is, the β-ray 64A is not emitted to the outside.

On the other hand, β-ray 64B emitted from the tritium 62B reaches the scintillator plate 58. However, a certain attenuation occurs before the β-ray 64B reaches the scintillator plate 58, and, even if light emission is caused at the scintillator plate 58, light 66 emitted to the outside by the light emission would be weak. In this manner, there is a limit to the measurement in the state of liquid sample, for the measurement of the low energy β-ray emitting nuclides. On the contrary, with the use of the above-described method of the present disclosure, the low energy β-ray can be measured with high sensitivity without being restricted by such a limitation.

Next, a first configuration of a radiation measurement method according to an embodiment of the present disclosure will be described with reference to FIG. 5. The radiation measurement method of the first configuration is automatically executed by the radiation measurement apparatus shown in FIG. 1. Alternatively, a part or all of the steps may be executed manually.

Figure 5:
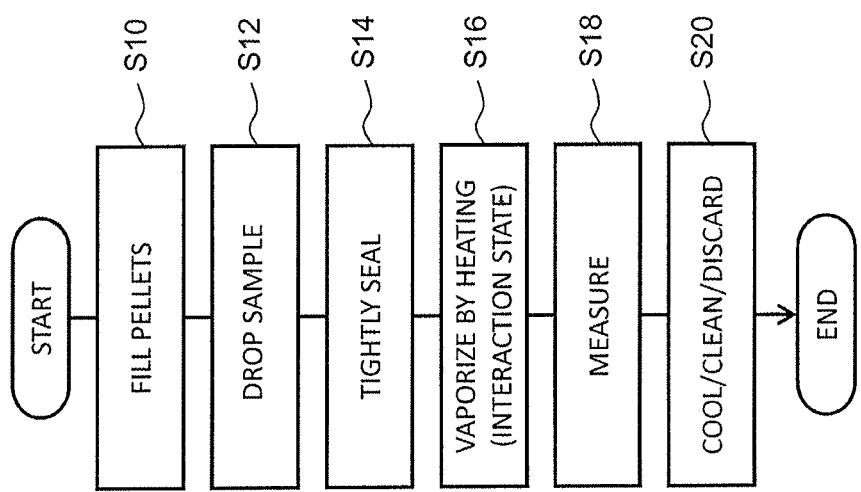
FIG. 5 is a flowchart showing a first configuration of a radiation measurement method according to an embodiment of the present disclosure.
Figure 6:
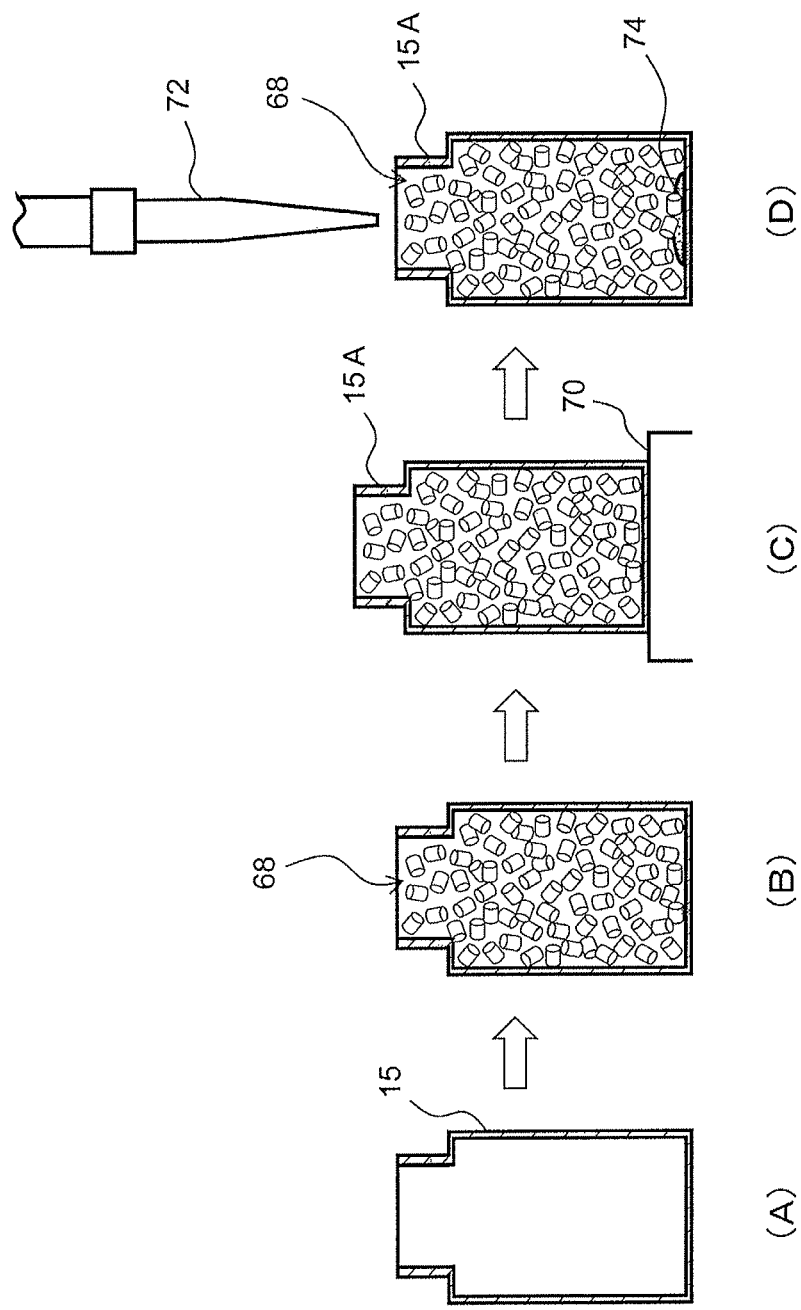
FIG. 6 is a diagram showing a filling step and a sample introduction step.

In S10 of FIG. 5, as shown in a state (A) of FIG. 6, first, an empty container body 15 is prepared, and as shown in a state (B) in FIG. 6, a plurality of pellets are inserted into the container body 15. With this process, a collective structure 68 of the pellets is formed. Then, as shown in a state (C) of FIG. 6, weight of the container body 15A including the pellet collective structure 68 is measure using a weight sensor 70 as necessary. For example, the measurement value determined by the weight sensor is taken into consideration in specifying the conversion efficiency or the like. Alternatively, in place of inserting the pellet to the uppermost part of the internal space of the container body 15, the pellet may be inserted up to a level at which the pellet is not hidden by the lid at the final state.

In S12 of FIG. 5, as shown in a state (D) of FIG. 6, a predetermined amount of a sample is introduced into the container body 15A using, for example, a manual pipet or an automatic dispenser device having a pipet (nozzle). In a state (D), a nozzle 72 for introducing the sample is shown. On a bottom surface of the container body 15A, a dropped sample 74 is present. When a small amount of the sample is dropped, a state where the sample is adhered to surfaces of a plurality of pellets is formed. In this case, the sample does not necessarily reach the bottom surface. The amount of sample is desirably determined based on a volume in the container, a volume of the scintillator member, a vaporization condition, an environmental temperature, or the like.

Figure 7:
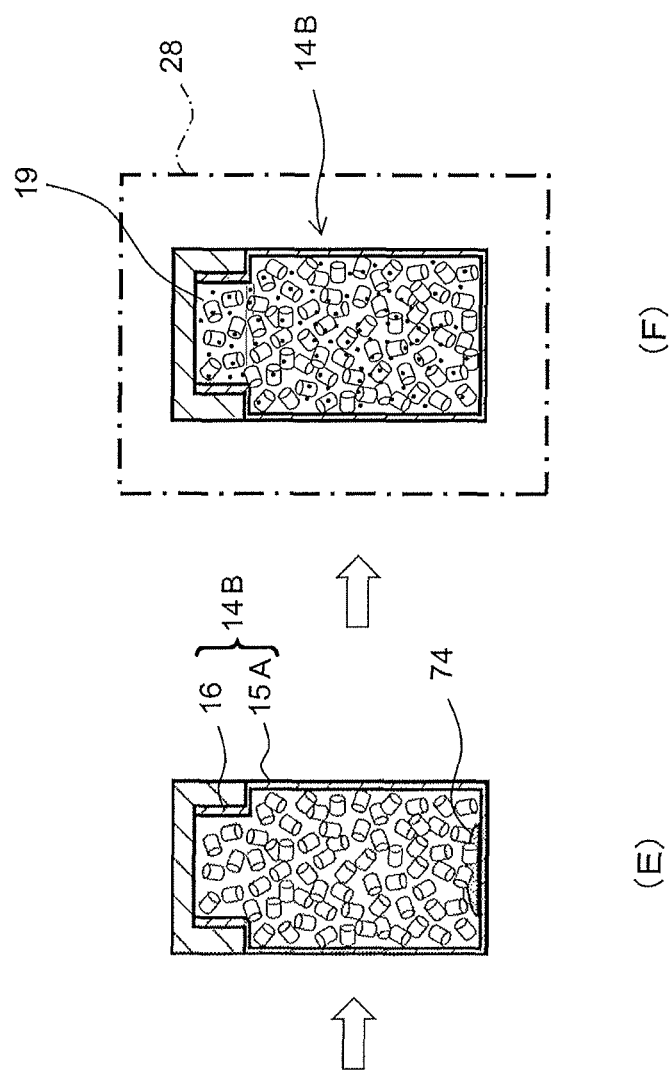
FIG. 7 is a diagram showing a tight sealing step and a vaporization step.

In S14 of FIG. 5, as shown in a state (E) of FIG. 7, the lid 16 is mounted on an opening of the container body 15A. With this process, a container 14B is formed. The internal space of the container 14B is a tightly sealed space. Alternatively, a process such as a tape wrapping may be applied as necessary, in order to further improve the airtightness between the container body 15A and the lid 16. Alternatively, a seal structure may be provided on the container itself.

In S16 of FIG. 5, as shown in a state (F) of FIG. 7, in this example configuration, the heater unit 28 is used to apply a heating process to the container 14B. With this process, the sample existing on the bottom surface of the container 14B is evaporated (vaporized), thus generating gas 19 made of a large number of particles. When the sample is adhered onto the surface of the plurality of pellets also, the gas 19 is generated. When the amount of dropped sample is small, the gas 19 may be generated by natural vaporization without even applying the heating process. In general, the plastic scintillator does not have much endurance against heat, and, from this point of view, it is desirable to heat with a relatively low temperature or to employ the method of natural vaporization. In the state (F), the plurality of particles are represented by a plurality of black dots. With this configuration, the interaction state is formed. With the vaporization, light emission is caused on the scintillator member.

In S18 of FIG. 5, the container is placed in the measurement chamber 12 as shown in FIG. 1, and the light caused by the scintillator member is detected by the pair of photomultiplier tubes. With this process, the calculation of concentration of the radioactive substance contained in the sample or the like is executed.

In S20 of FIG. 5, the container after the measurement is taken out from the measurement chamber, and cooling, cleaning, discarding, or the like are executed for the container. These processes are executed as necessary. The plurality of pellets after natural cooling may be taken out from the container and cleaned, or may be discarded without being cleaned. Alternatively, the container may be cleaned simultaneously with the cleaning of the plurality of pellets.

Figure 8:
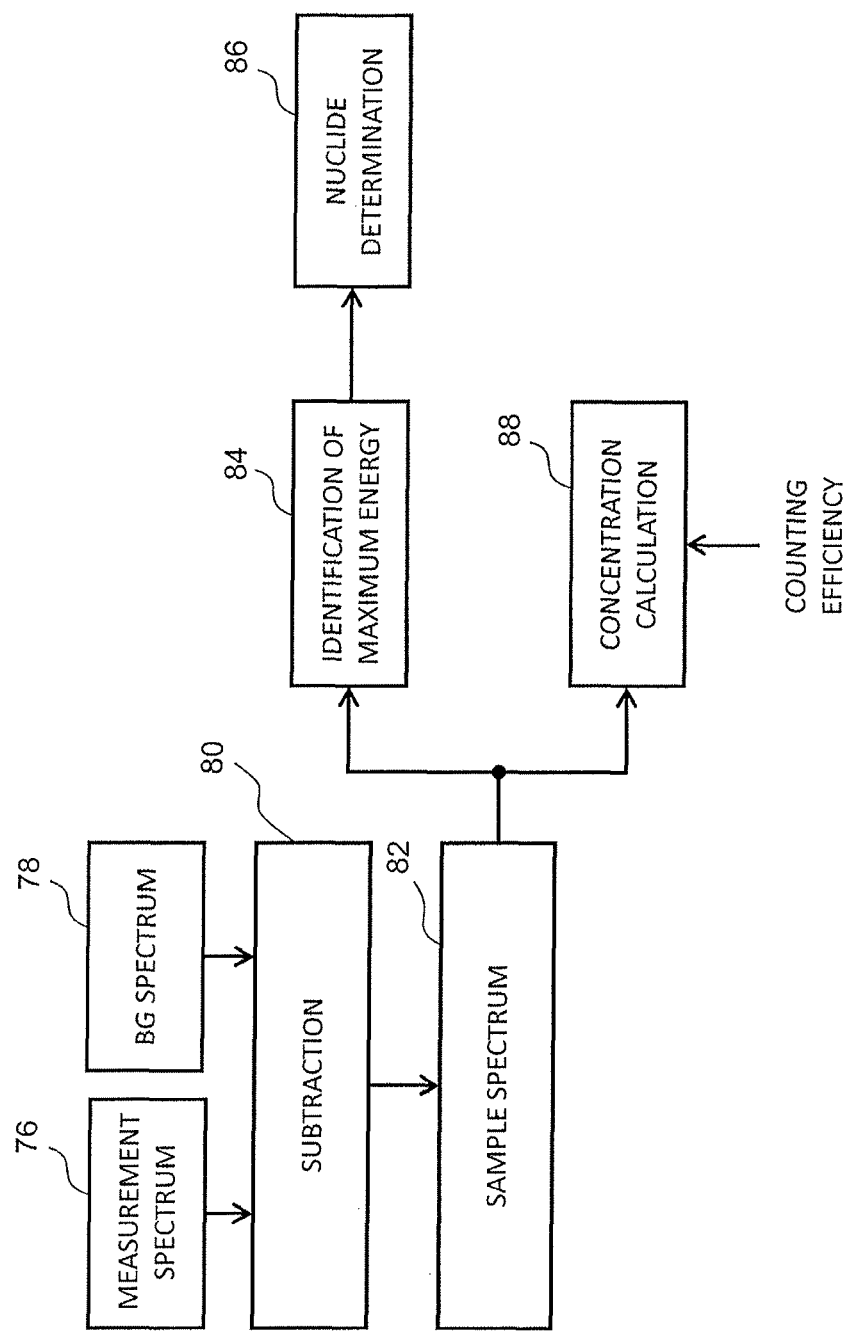
FIG. 8 is a diagram for explaining a spectrum calculation.

FIG. 8 shows an example calculation executed in the calculation controller shown in FIG. 1. A measurement spectrum 76 is a spectrum obtained by executing measurement on the container including the scintillator member and the gas. A background (BG) spectrum 78 is a spectrum which is obtained in a state where only the scintillator member is inserted into the container (without the liquid sample), and the container is placed in the measurement chamber. In a subtraction process 80, a process to subtract the BG spectrum 78 from the measurement spectrum 76 is executed. With this process, a sample spectrum 82 is obtained.

Based on the sample spectrum 82, as shown by reference numeral 84, a maximum energy is identified. Based on the maximum energy, determination of the nuclide is executed as shown by reference numeral 86, as necessary.

In addition, based on the sample spectrum 82, a concentration calculation of the radiation nuclide is executed as shown by reference numeral 88. In this case, the counting efficiency is taken into consideration as necessary. For example, the counting efficiency may be calculated based on information such as the amount of sample, the number of pellets, the volume inside the container, or the like. Alternatively, a table correlating these information and the counting efficiency may be prepared in advance. The calculation content shown in FIG. 8 is merely exemplary, and calculations other than those shown in the figure may be executed. In the liquid scintillator method of the related art, identification of the maximum energy has been difficult, but according to the present method, an advantage can be obtained in that the maximum energy can be easily identified. In addition, because the present method is not affected by chemical quenching or the like, a more accurate concentration calculation or the like can be executed, or a complicated calibration process becomes unnecessary.

Figure 9:
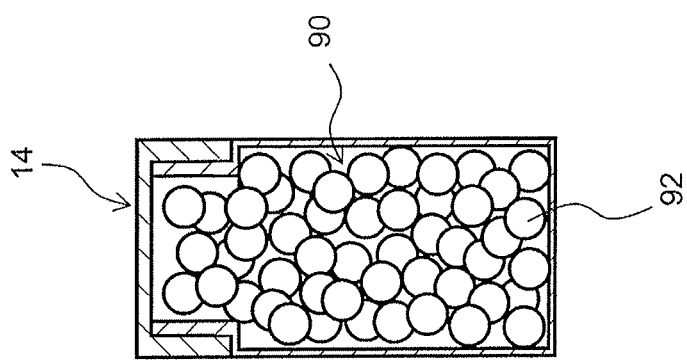
FIG. 9 is a diagram showing a second example configuration of a scintillator member.

FIG. 9 shows a second example configuration of the scintillator member. In this example configuration, in the container 14, a scintillator member 90 is provided which is a collective structure of a plurality of scintillator elements. The collective structure is formed from a spherical plastic scintillator 92. In the collective structure, a large number of gaps are formed inside the collective structure, which function as a flow path network for flow of the gas. In other words, by employing such a gap structure, a surface area of the scintillator member 90 can be increased, and, thus, an area in which the interaction with the particle (that is, the gas particle) occurs can be increased. In either case, the form of the scintillator element is desirably determined such that a gap structure is formed inside the collective structure when the collective structure is formed.

By employing a method of filling the container 14 with the plurality of scintillator elements, it becomes possible to eliminate the dead space in the container, and an advantage can thus be obtained in that a collective structure form matching the form of the internal space of the container 14 can be naturally constructed.

Figure 10:
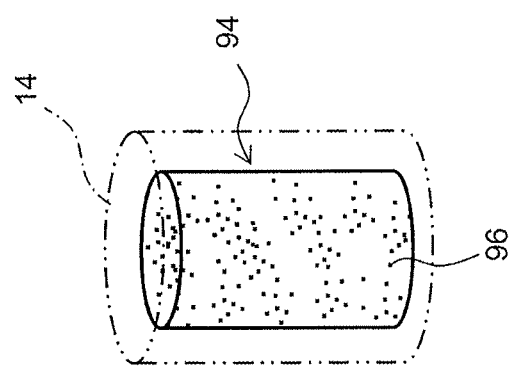
FIG. 10 is a diagram showing a third example configuration of a scintillator member.

FIG. 10 shows a third example configuration of the scintillator member. In the container 14, a scintillator member 94 having a circular tube shape is placed. The scintillator member 94 has a porous structure or a sponge structure, and a large number of gaps 96 exist in the scintillator member 94.

Figure 11:
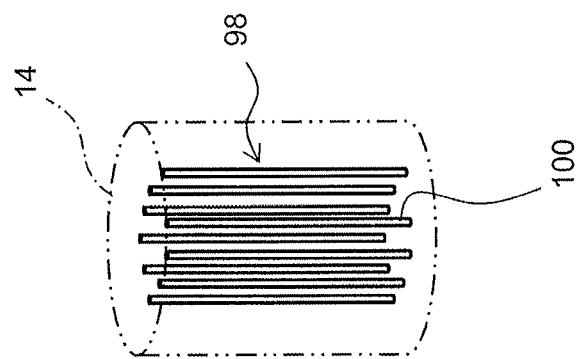
FIG. 11 is a diagram showing a fourth example configuration of a scintillator member.

FIG. 11 shows a fourth example configuration of the scintillator member. In the container 14, a scintillator member 98 is placed, which is formed from a plurality of scintillator fibers 100. A gas flow path exists between individual fibers, and in the scintillator member 98 as a whole, a plurality of gas flow paths exist inside the scintillator member 98. Alternatively, an individual fiber may be formed as a hollow structure.

Figure 12:
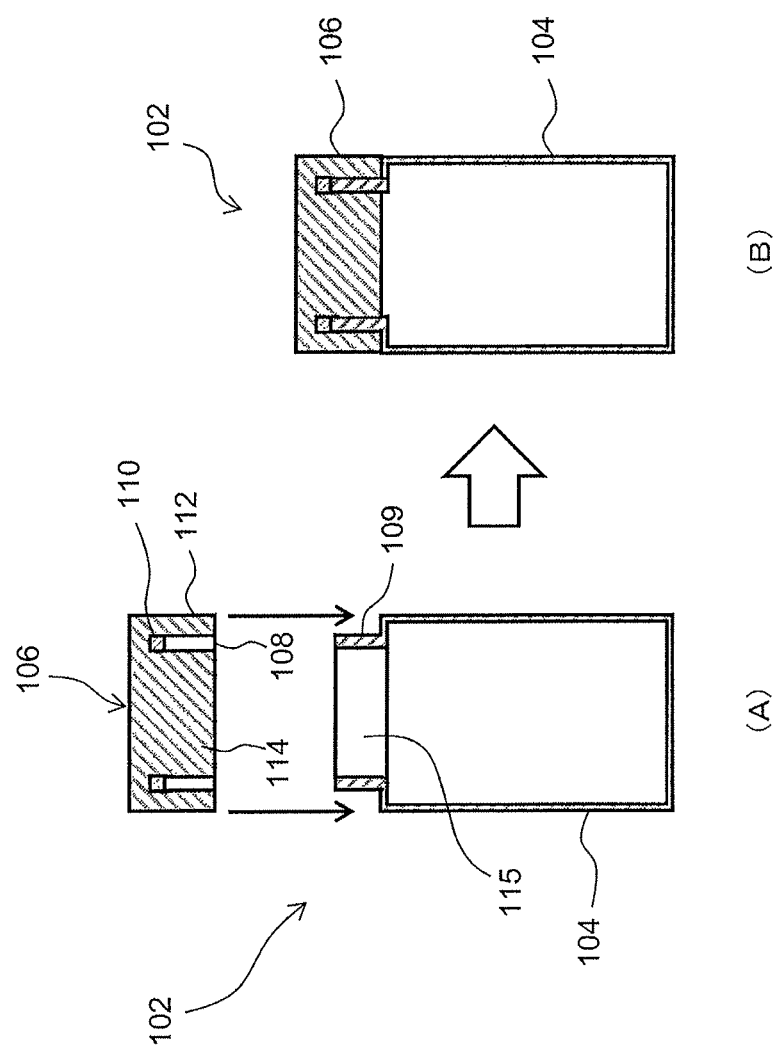
FIG. 12 is a diagram showing a second example configuration of a container.

FIG. 12 shows a second example configuration of the container. As a state (A) of FIG. 12, a state where a cap 106 is detached from a container body 104 is shown. The container body 104 has a tubular portion 109 on its upper part, which forms an opening. Inside the tubular portion 109 is an upper space 115. Meanwhile, in the cap 106, a ring-shaped grove 108 is formed corresponding to the tubular portion 109, and a ring-shaped packing 110 is placed at the deepest position of the groove 108; that is, on the ceiling side. An outer side of the ring-shaped groove 108 is an outer portion 112, and an inner side of the groove 108 forms an inner portion 114, which protrudes toward the side of the container body 104 (that is, in the downward direction).

As shown in a state (B) of FIG. 12, when the cap 106 is mounted on the container body 104, a space therebetween is completely sealed by an action of the packing 110. At the same time, the upper space 115 produced at the side of the container body 104 is substantially filled by the inner portion 114, and an advantage can be obtained in that the dead space generated at the upper part in the container 102 can be eliminated or a portion with inferior light detection efficiency can be eliminated. Alternatively, other container structures may be employed.

Figure 13:
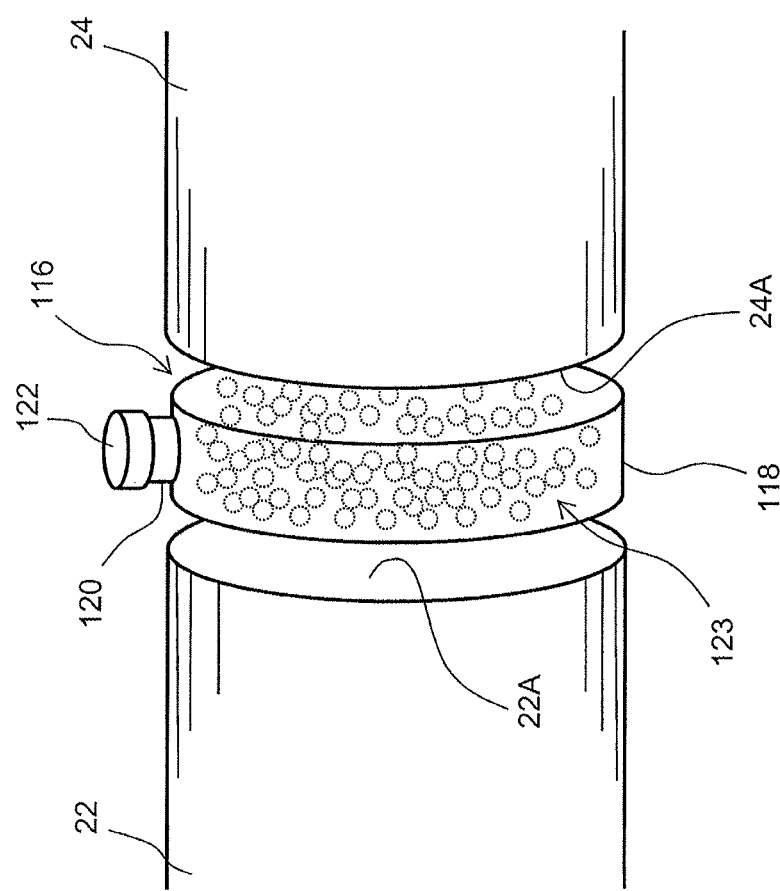
FIG. 13 is a diagram showing a third example configuration of a container.

FIG. 13 shows a third example configuration of the container. A container 116 has a disk shaped body 118 and a cap 122 which seals an opening 120 formed on the body 118. The inside of the body 118 forms an internal space, and a scintillator member 123 is placed therein. The scintillator member 123 is formed from a plurality of scintillator elements. In the internal space, gas is stored along with the scintillator member 123 as described above, and an interaction state is thus constructed. The pair of photomultiplier tubes 22 and 24 are provided to oppose the respective side surfaces of the body 118. Specifically, one side surface of the body 118 is proximate to and opposes the light-receiving surface 22A, and the other side surface of the body 118 is proximate to and opposes the light-receiving surface 24A. According to the structure shown in FIG. 13, the light generated at a center portion of the container 116 can also be effectively detected. In particular, because the shape and size of the side surface of the body 118 match the size and form of the pair of light-receiving surfaces 22A and 24A, an advantage can be obtained in that the measurement efficiency can be improved.

Next, a cleaning method will be described with several example configurations.

FIG. 14 shows a first example configuration of the cleaning method. A container 124 comprises a container body 126 and a cap 128, and in this example configuration, a first nozzle 132 and a second nozzle 134 which penetrate through the cap 128 are provided. A lower end of the first nozzle 132 is positioned at an upper part in the internal space of the container, and a lower end 136 of the second nozzle 134 is positioned at a lower part in the internal space. The cap 128 may be a cap dedicated for cleaning, or may be a cap which is used during the measurement.

In the structure shown in FIG. 14, by supplying a cleaning solution to the inside of the container 124 from the first nozzle 132 and suctioning from the second nozzle 134, it is possible to clean the inside of the container and the scintillator member 130. After the cleaning with the cleaning solution, for example, a rinsing process may be applied using distilled water.

Alternatively, as shown in a second example configuration of FIG. 15, the container 124 may be set in an upside-down position, and, in this state, the cleaning solution may be supplied to the inside of the container 124 from the second nozzle 134 and suctioning of the cleaning solution may be executed at the first nozzle 132. By executing a background measurement on the scintillator member after cleaning, the effect of the cleaning can be checked.

FIG. 16 shows a third example configuration of the cleaning method. In this example configuration, the scintillator member (group of pellets 137) is taken out from the measurement container, and is inserted to the inside of a cleaning tank 135. A cleaning solution 140 is supplied into the cleaning tank 135 by a nozzle 138. After necessary stirring and cleaning processes or the like are executed, a valve 142 provided on a drain path 141 is opened to drain the cleaning solution. Then, a rinsing process or a drying process or the like is executed on the remaining group of pellets 137. A filter 144 is provided on the drain path 141 to prevent discharge of the pellets.

As described above, the cleaning process can be executed while the group of pellets is stored within the container or while the group of pellets is taken out from the container. Alternatively, the group of pellets may be discarded at every measurement. According to the configurations shown in FIGS. 14 and 15, an advantage can be obtained in that the inside of the container can be cleaned at the same time as the cleaning of the group of pellets.

FIG. 17 shows a second example configuration of a radiation measurement method according to an embodiment of the present disclosure. In S30, pellets are filled in the container. In S32, a lid is mounted on the container to form a tightly sealed state. In S34, air is suctioned out from the internal space of the container so that the inside of the container is set at a reduced pressure state; that is, a negative pressure state. This process may be considered to be a vaporization promoting process. In S36, a sample is introduced into the container. In S38, the sample is naturally vaporized to generate gas. In this case, heating or the like may be executed in order to further promote vaporization. In S40, in the interaction state where the gas is confined in the container along with the scintillator member, light generated by the scintillator member is detected. In S42, a necessary cleaning process and discard process are executed.

FIG. 18 shows a third example configuration of a radiation measurement method according to an embodiment of the present disclosure. In S50, pellets are filled in the container. In S52, the container is set in a tightly sealed state. In addition, in S54, gas is produced by a vaporization process of the liquid sample at an outside of the container.

In S56, the gas is introduced to the inside of the container in the tightly sealed state through a pipe or the like. The interaction state in which the gas is confined along with the scintillator member is formed in the container, and, in this state, light generated by the scintillator member is measured in S58. In S60, a necessary cleaning process and discard process are executed.

Figure 19:
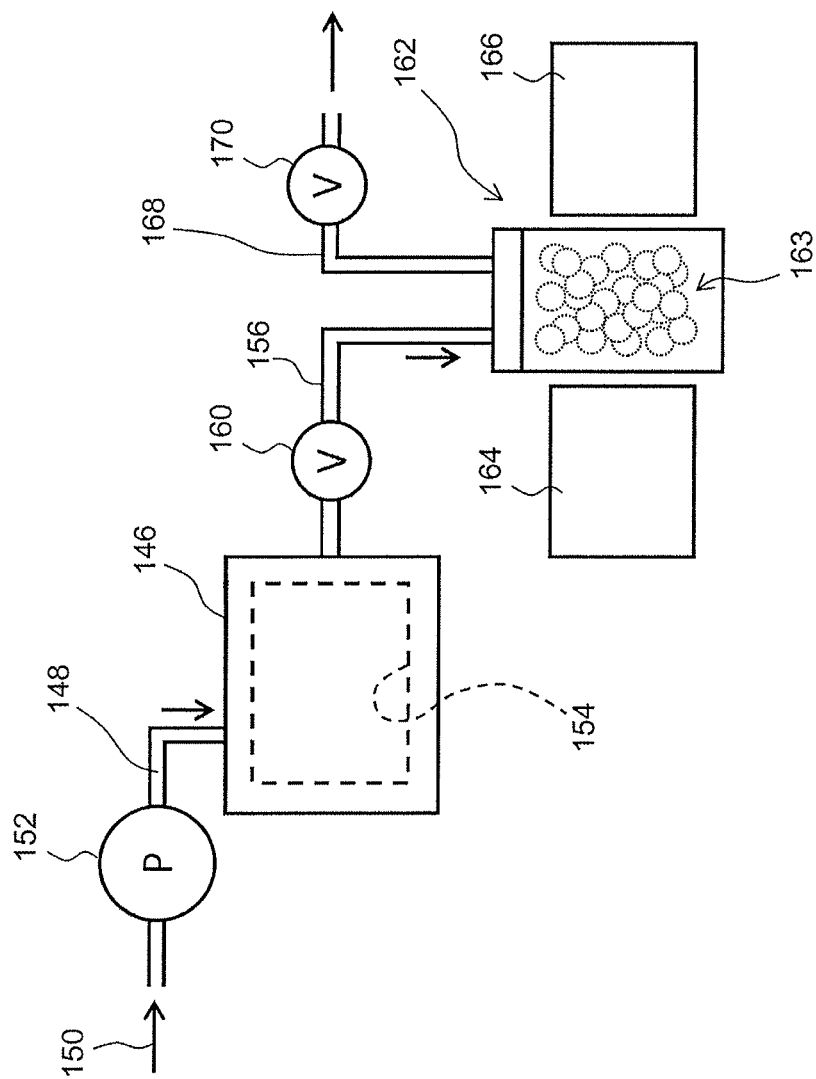
FIG. 19 is a diagram showing an alternative configuration in which a vaporization process is executed outside the container.

FIG. 19 shows a second example configuration of a radiation measurement apparatus according to an embodiment of the present disclosure. A liquid sample 150 is introduced to a vaporization tank 146 through a pipe 148. In this process, a pump 152 is used. A heater 154 is provided in the vaporization tank 146, and gas is generated by vaporizing the liquid sample. The gas is sent to the inside of a container 162 through the pipe 152 via a valve 160.

A scintillator member 163 is provided in the container 162, and, when gas is introduced into the container 162, the interaction state as described above is formed, and light emission is caused at the scintillator member 163. The light is then detected by a pair of photomultiplier tubes 164 and 166. Gas after the measurement is discharged to the outside through a pipe 168 and by an action of a valve 170. Alternatively, light detection; that is, radiation detection, can be continuously executed while forming a state where the gas is circulated to the inside of the container 162.

Figure 20:
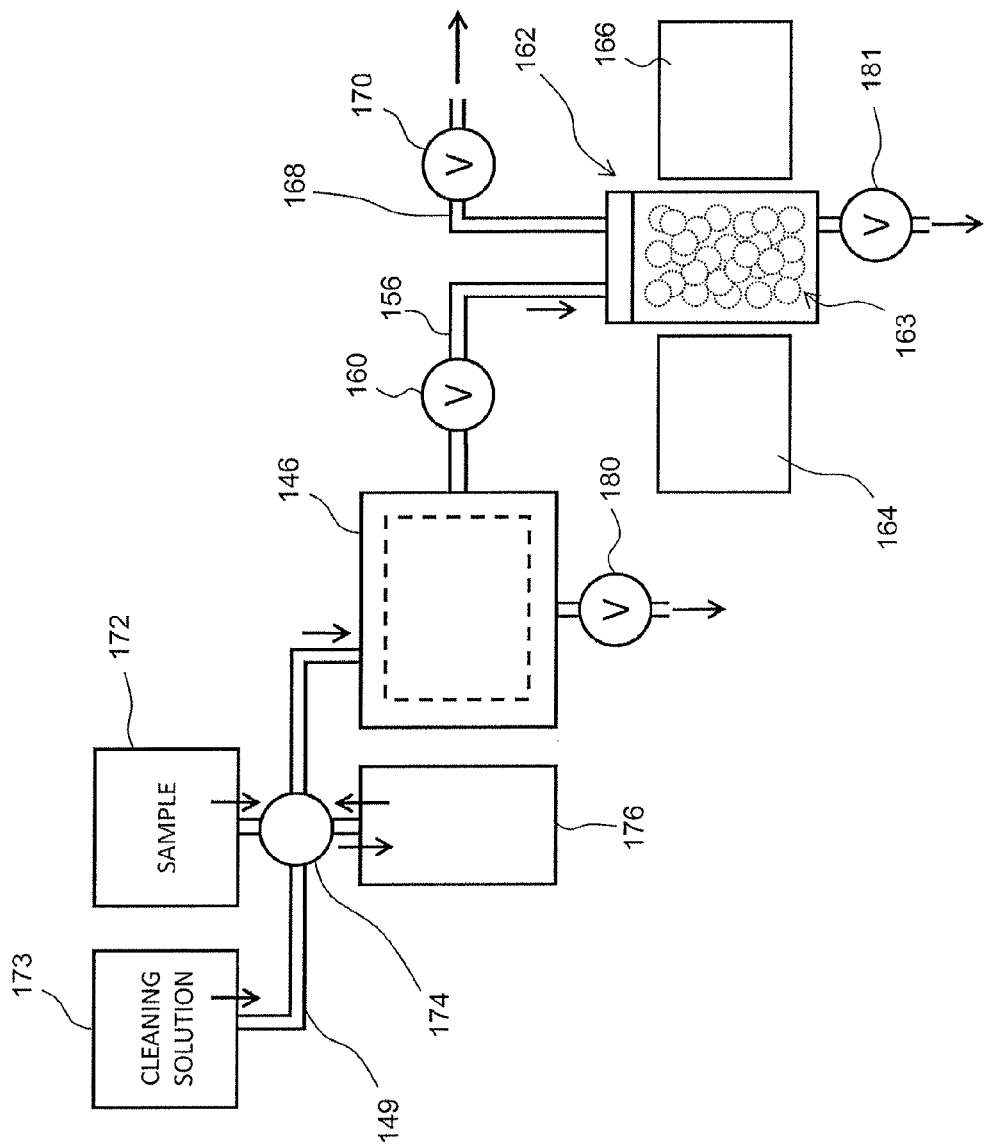
FIG. 20 is a diagram showing an alternative configuration having a cleaning mechanism.

FIG. 20 shows a third example configuration of a radiation measurement apparatus according to an embodiment of the present invention. A liquid sample is stored in a tank 172, is once captured by a syringe pump 176 via a valve 174, and is sent from the syringe pump 176 via the valve 174 to a vaporization tank 146. Gas generated by a vaporization process in the vaporization tank 146 is sent to the inside of a container 162 via a pipe 156. A scintillator member 163 is provided in the container 162. A pipe 168 is a path for discharging the sample gas. A valve 160 is provided on the pipe 156. A valve 170 is provided on the pipe 168.

In the example configuration shown in FIG. 20, a tank 173 for cleaning solution is provided, and, after the measurement is completed, a cleaning solution is captured by the syringe pump 176 and then sent via a pipe 149 to the vaporization tank 146. With this process, the vaporization tank 146 is filled with the cleaning solution. In addition, the cleaning solution is also sent to the inside of the container 162 via the pipe 156, and the inside of the container 162 is also filled with the cleaning solution. By cleaning the individual structure while forming a circulation state of the cleaning solution, and opening valves 180 and 181 at the end, it becomes possible to discharge the cleaning solution from the vaporization tank 146 to the outside and to discharge the cleaning solution from the container 162 to the outside. In this manner, by incorporating the cleaning system in the pipe paths, it becomes possible to repeatedly use the container and the scintillator member while cleaning the container and the scintillator member. After the cleaning, light detection for the container may be executed using a pair of photomultiplier tubes 164 and 166 as necessary. That is, it is possible to check the cleaning result by executing the background measurement.

The example configurations shown in FIGS. 19 and 20 are merely exemplary, and various configurations may be employed according to the objective, usage, or the like. In the above-described embodiment, measurement with regard to tritium is executed, but alternatively, other low energy β-ray emitting nuclides may be set as the measurement target. Alternatively, other types of radiation may be set as the measurement target.

The invention claimed is:

1. A radiation measurement method comprising:
a state formation step in which a liquid sample containing a radioactive substance is vaporized to generate gas containing a plurality of particles, and the gas is confined along with a solid scintillator member in a space isolated from the outside environment, to form an interaction state; and
a detection step in which light generated on the scintillator member due to radiation from the plurality of particles in the interaction state is detected.

2. The radiation measurement method according to claim 1, wherein
the scintillator member has a gap structure including a plurality of gaps that can capture the plurality of particles.

3. The radiation measurement method according to claim 2, wherein
a container having an internal space serving as the space is used,
the scintillator member is a collective structure of a plurality of scintillator elements filled in the container, and the collective structure has, as the gap structure, a flow path network through which the gas flows.

4. The radiation measurement method according to claim 3, wherein
the state formation step comprises:
a collective structure filling step in which the plurality of scintillator elements are introduced into the container;
a sample introduction step in which the liquid sample is introduced into the container;
a tightly sealing step in which the container into which the plurality of scintillator element and the liquid sample are introduced is set to a tightly sealed state; and
a vaporization step in which vaporization of the liquid sample is caused in the container in the tightly sealed state.

5. The radiation measurement method according to claim 4, wherein
the vaporization step comprises a heating step in which the liquid sample is heated.

6. The radiation measurement method according to claim 1, further comprising, after the detection step, a cleaning step in which the scintillator member is cleaned.

7. The radiation measurement method according to claim 1, wherein
the radioactive substance includes tritium which emits β-ray as the radiation.

8. A radiation measurement apparatus comprising:
a vaporizer unit that vaporizes a liquid sample containing a radioactive substance to generate gas containing a plurality of particles;
a container that stores a solid scintillator member and the gas; and
a detector that detects light generated on the scintillator member due to radiation from the plurality of particles.

9. The radiation measurement apparatus according to claim 8, wherein
the scintillator member is a collective structure of a plurality of scintillator elements filled in the container.

10. The radiation measurement apparatus according to claim 9, wherein
each of the scintillator elements has a form that forms a plurality of gaps within the collective structure in a formed state of the collective structure.

11. The radiation measurement apparatus according to claim 10, wherein
each of the scintillator elements comprises a plastic scintillator.

12. The radiation measurement apparatus according to claim 8, wherein
the vaporizer unit is a unit that vaporizes the liquid sample in the interior of the container to generate the gas.

13. The radiation measurement apparatus according to claim 8, wherein
the vaporizer unit is a unit that vaporizes the liquid sample at an outside of the container to generate the gas, and
a mechanism is provided that introduces the gas generated at the outside of the container into the container.

* * * * *

UNITED STATES PATENT AND TRADEMARK OFFICE
CERTIFICATE OF CORRECTION

PATENT NO. : 9,958,563 B2  
APPLICATION NO. : 15/327080  
DATED : May 1, 2018  
INVENTOR(S) : Etsuko Furuta, Yuka Kato and Kiyoshi Ogiwara Page 1 of 1

It is certified that error appears in the above-identified patent and that said Letters Patent is hereby corrected as shown below:

On the Title Page

Replace item (73) with the following:
--(73) Assignees: OCHANOMIZU UNIVERSITY, Tokyo (JP);
                Hitachi, Ltd., Tokyo (JP).--

Signed and Sealed this  
Twenty-sixth Day of June, 2018

Andrei Iancu  
*Director of the United States Patent and Trademark Office*